(12) United States Patent
Hine et al.

(10) Patent No.: US 7,031,777 B2
(45) Date of Patent: Apr. 18, 2006

(54) CARDIAC VEIN LEAD WITH FLEXIBLE ANODE AND METHOD FOR FORMING SAME

(75) Inventors: Douglas S. Hine, White Bear Lake, MN (US); John L. Sommer, Coon Rapids, MN (US); Wayne R. Bass, Coon Rapids, MN (US); Mary M. Morris, Mounds View, MN (US); Peter B. McIntyre, Mounds View, MN (US); Carla C. Pfeiffer, Anoka, MN (US); Roger Lafond, Fridley, MN (US); Patricia K. Peterson, Centuria, WI (US)

(73) Assignee: Medtronic, Inc., Minneapolis, MN (US)

( * ) Notice: Subject to any disclaimer, the term of this patent is extended or adjusted under 35 U.S.C. 154(b) by 445 days.

(21) Appl. No.: 10/256,353

(22) Filed: Sep. 27, 2002

(65) Prior Publication Data

US 2004/0064173 A1   Apr. 1, 2004

(51) Int. Cl.
*A61N 1/05* (2006.01)

(52) U.S. Cl. .................. 607/122; 607/119; 607/123
(58) Field of Classification Search ......... 607/119–123
See application file for complete search history.

(56) References Cited

U.S. PATENT DOCUMENTS

| | | | |
|---|---|---|---|
| 4,355,646 A | 10/1982 | Kallok et al. ............... 128/786 |
| 4,506,680 A | 3/1985 | Stokes ......................... 128/786 |
| 4,944,088 A | 7/1990 | Doan et al. .................... 29/858 |
| 4,972,848 A | 11/1990 | Di Domenico et al. ..... 128/785 |
| 5,246,014 A | 9/1993 | Williams et al. ............. 607/122 |
| 5,342,414 A | 8/1994 | Mehra .......................... 607/127 |
| 5,466,254 A | 11/1995 | Helland ........................ 607/123 |
| 5,584,873 A | 12/1996 | Shoberg et al. .............. 607/122 |
| 5,676,694 A | 10/1997 | Boser et al. .................. 607/122 |
| 5,871,530 A * | 2/1999 | Williams et al. ............. 607/122 |
| 5,928,277 A * | 7/1999 | Laske et al. .................. 607/122 |
| 5,935,160 A | 8/1999 | Auricchio et al. ........... 607/122 |
| 6,141,593 A | 10/2000 | Patag .......................... 607/122 |
| 6,192,280 B1 | 2/2001 | Sommer et al. .............. 607/122 |
| 6,295,476 B1 * | 9/2001 | Schaenzer .................... 607/122 |
| 6,321,123 B1 | 11/2001 | Morris et al. ................ 607/122 |
| 6,456,888 B1 * | 9/2002 | Skinner et al. .............. 607/116 |
| 2002/0016622 A1 | 2/2002 | Janke et al. | |
| 2002/0077685 A1 | 6/2002 | Sundquist et al. | |

* cited by examiner

*Primary Examiner*—Carl Layno
(74) *Attorney, Agent, or Firm*—Michael C. Soldner; Girma Wolde-Michael

(57) ABSTRACT

A bipolar cardiac vein lead and method of assembly is provided wherein the lead includes a flexible coil anode electrode such that the lead may be advanced through a tortuous pathway. The coil electrode is coupled to a conductor using a method of assembly that minimizes or eliminates rigid components, maintaining flexibility of the distal lead end. Multi-polar cardiac vein leads may include multiple flexible coil electrodes to achieve pacing and/or sensing in the left atrium and the left ventricle or at multiple left heart sites.

15 Claims, 6 Drawing Sheets

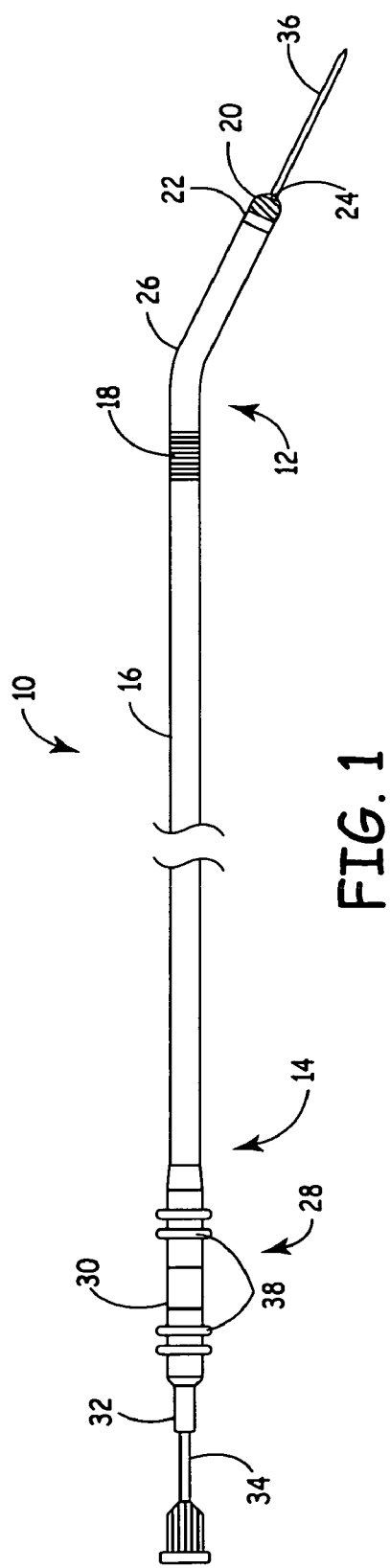
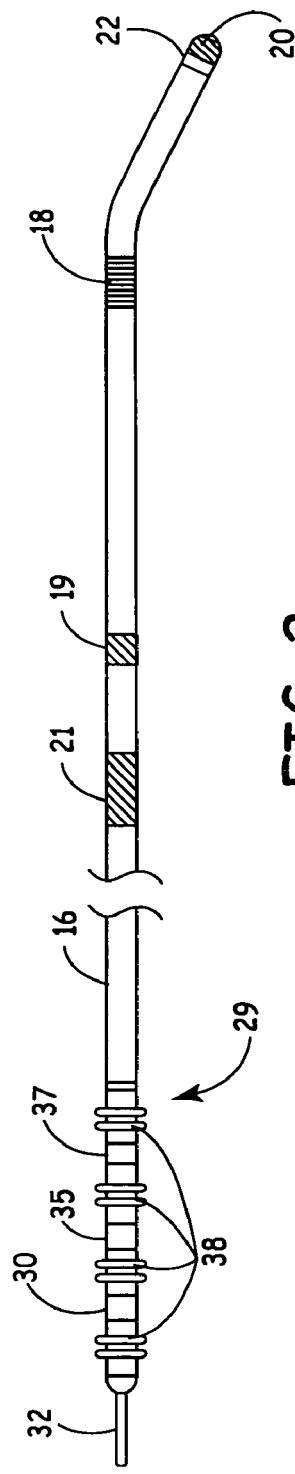

CARDIAC VEIN LEAD WITH FLEXIBLE ANODE AND METHOD FOR FORMING SAME

FIELD OF THE INVENTION

The present invention generally relates to medical electrical leads, and more particularly, the present invention relates to a cardiac vein lead having a flexible electrode design to allow advancement of the lead through a tortuous pathway to a desired implant site.

BACKGROUND OF THE INVENTION

Coronary sinus leads have been developed to achieve cardiac sensing, pacing and defibrillation in the left heart chambers. Examples of coronary sinus leads are disclosed in U.S. Pat. No. 6,321,123 B1 issued to Morris et al., and U.S. Pat. No. 5,466,254 issued to Helland. Small diameter leads that may be advanced further into the cardiac veins have been developed in order to more specifically target the left ventricle for pacing and/or sensing.

Coronary sinus and cardiac vein leads are generally implanted with the use of a guide catheter and/or a guidewire or stylet to achieve proper placement of the lead. A cardiac vein lead may be placed using a multi-step procedure wherein a guide catheter is advanced into the coronary sinus ostium and a guidewire is advanced further through the coronary sinus and great cardiac vein to a desired cardiac vein branch. Because the tip of a guidewire is generally flexible and may be pre-shaped in a bend or curve, the tip of the guidewire can be steered into a desired venous branch. A cardiac vein lead may therefore be advanced to a desired implant location relative to the left ventricle using a guidewire extending entirely through the lead and out a distal end of the lead.

Cardiac leads generally need to be highly flexible in order to withstand flexing motion caused by the beating heart without fracturing. A stiff stylet or guidewire provides a flexible lead with the stiffness needed to advance the lead through a venous pathway. Leads having a hollow lumen to allow deployment using a guide wire or stylet are often referred to as "over-the-wire" leads. Once the lead is placed in a desired location, the guidewire or stylet may be removed. A guidewire placed implantable lead is disclosed in U.S. Pat. No. 6,192,280, issued to Sommer, et al. A coronary vein lead having a flexible tip and which may be adapted for receiving a stylet or guidewire is disclosed in U.S. Pat. No. 5,935,160, issued to Auricchio et al.

Cardiac vein leads are particularly difficult to implant due to the tortuous pathway encountered as the lead is advanced through the cardiac veins. Placement of a cardiac vein lead in a desired venous branch may require angling the lead end greater than ninety degrees in order to maneuver the lead into a desired position. Some cardiac vein locations may therefore be inaccessible due to limitations and difficulties associated with maneuvering currently available lead systems into a narrow venous branch at an oblique, or even acute, angle.

In order to provide the flexibility needed to maneuver a cardiac vein lead to a desired implant site, cardiac vein leads have been manufactured as unipolar leads equipped with a tip electrode but lacking a ring electrode, which is conventionally a rigid structure and limits the flexibility of the distal lead end. However, since bipolar pacing and/or sensing is often preferred over unipolar pacing and/or sensing, it is desirable to provide a bipolar cardiac vein lead that possesses the flexibility needed to guide the through a tortuous pathway. It is further desirable to limit the number of rigid parts required for assembling a bipolar cardiac vein lead to maintain flexibility, ease manufacturing, and reduce cost.

SUMMARY OF THE INVENTION

The present invention provides a medical electrical lead having a flexible electrode design and a method of manufacture that minimizes rigid parts. The medical lead may include a tip electrode and any number of flexible coil electrodes mounted proximally to the tip electrode on the lead body. In a preferred embodiment, a flexible coil electrode is provided as an anode for bipolar pacing and/or sensing in conjunction with a cathode tip electrode. In other embodiments, a flexible coil electrode may be spaced from the distal end of the lead such that it may serve as a cathode for left atrial pacing and/or sensing when the distal lead end is positioned deep in a cardiac vein for left ventricular pacing. Multiple flexible coil electrodes may be provided for stimulation and/or sensing at multiple sites in the left heart in either bipolar or unipolar configurations.

The flexible coil electrode is preferably formed from a bifilar platinum iridium coil and is electrically coupled to a conductor extending to a proximal connector assembly. The coil electrode may be coupled to a conductor via a conductive sleeve. Alternatively, the coil electrode may overlap a coiled conductor, and the two may be joined by welding. In yet another embodiment, a coiled conductor, preferably formed from platinum iridium clad tantalum, may extend from an outer insulation sheath. The exposed area of the coiled conductor may then serve as a flexible coil electrode.

The distal end of the coil electrode may be finished by sculpt welding the filar ends to an adjacent filar. The distal end of the coil electrode may alternatively be finished by compressing the filars and joining them to each other in a continuous radial weld. A molybdenum mandrel is preferably used during this welding process to prevent contamination of the weld pool.

The flexible coil electrode design allows a bipolar or multipolar cardiac vein lead to be constructed having a flexible distal end allowing the lead to be delivered via catheter delivery and/or guidewire delivery systems through a tortuous pathway. Methods of manufacture limit the number of components and rigid structures required for assembly, thereby maintaining lead flexibility, easing manufacturing processes, and reducing cost.

BRIEF DESCRIPTION OF THE DRAWINGS

FIG. 1 is a plan view of a bipolar cardiac vein lead having a flexible coil anode electrode in accordance with the present invention.

FIG. 2 illustrates a multi-polar cardiac vein lead having a tip electrode and three flexible coil electrodes for achieving bipolar pacing and/or sensing in the left ventricle and the left atrium.

DETAILED DESCRIPTION OF THE INVENTION

Figure 3:
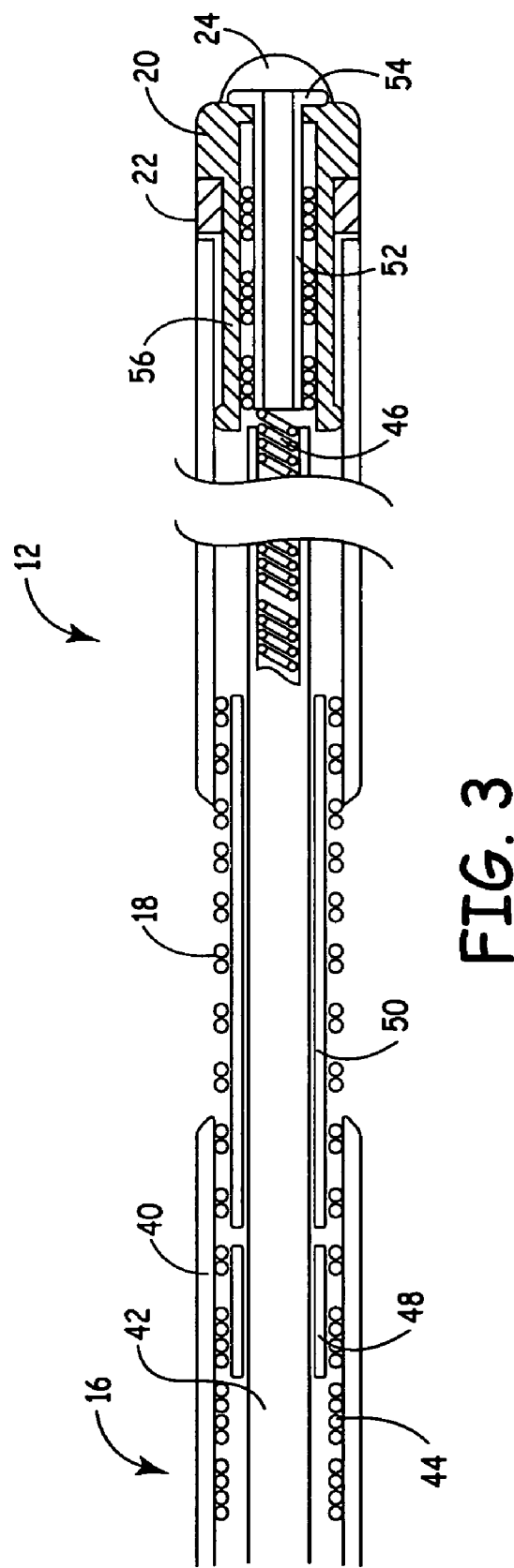
FIG. 3 is a side, cut-away view of a distal end of a lead having a flexible coil electrode in accordance with the present invention.

FIG. 1 is a plan view of a bipolar cardiac vein lead having a flexible coil anode electrode in accordance with the present invention. As illustrated in FIG. 1, according to the present invention, a lead 10 includes a flexible, elongated lead body 16 extending between a proximal end 14 and a distal end 12, and a tip electrode 20 positioned at distal lead end 12. Tip electrode 20 is shown in FIG. 1 as being a ring tip electrode and may resemble the ring tip electrode disclosed in U.S. Pat. No. 5,342,414 issued to Mehra, incorporated herein by reference in its entirety. However, tip electrode 20 may alternatively be provided as a generally hemispherical electrode, a helical electrode, a barb or any other tip electrode known for use in cardiac leads. A monolithic controlled release device (MCRD) 22 may optionally be provided proximal to tip electrode 20 to elute an anti-inflammatory steroid to prevent degradation of the electrical properties at the electrode-tissue interface due to the body's inflammatory response. MCRD 22 may be provided as generally disclosed in U.S. Pat. No. 4,506,680 issued to Stokes or U.S. Pat. No. 4,972,848 issued to DiDomenico et al., both patents incorporated herein by reference in their entirety.

A seal 24 may be provided at the distal end of lead 10 to prevent the ingress of body fluids into lead body 16, which can pose a risk for infection. Seal 24 may be generally cup-shaped and may be provided as described in U.S. Pat. No. 6,192,280 issued to Sommer et al., incorporated herein by reference in its entirety. Alternatively, the seal 24 can be fabricated such that seal 24 is entirely contained within the distal end of the lead 10. Alternative embodiments of a seal at or near the distal end of a medical lead or medical device that may be adapted for use with the present invention are disclosed in U.S. Pat. Application Ser. No. 20020016622 to Janke et al., and U.S. Pat. Application Ser. No. 20020077685 to Sundquist et al., both of which are incorporated herein by reference in their entirety, Other types of seals for preventing fluid from entering a tubular body of a medical device may also be used.

An anode coil electrode 18 is spaced along lead body 16 spaced proximally from tip electrode 20. Coil electrode 18 is preferably formed from a bifilar platinum iridium coil, though a multi-filar coil could also be used. A single filar coil electrode is conceivable, however, a bifilar or multi-filar coil provides redundancy, maintaining lead functionality should one filar fracture. Coil electrode 18 may be formed from any biocompatible conductive material, such as platinum, iridium, titanium, or alloys thereof. Coil 18 may be formed from wire that is generally round in cross-section or flat wire.

In the embodiment shown in FIG. 1, coil electrode 18 is intended to serve as an anode electrode paired with the cathode tip electrode 20 for bipolar pacing and/or sensing. Anodal stimulation may also be achieved through coil electrode 18 when the energy of a delivered pacing pulse is adequately high. The length of coil electrode 18 is selected based on a desired electrode surface area suitable for the intended purpose and considering other design factors such as coil diameter, coil pitch, the surface area of each coil winding, etc. For example, an acceptable surface area for an anode coil electrode is approximately 30 to 40 square millimeters when used in conjunction with a cathode tip electrode having a surface area of approximately 5 to 6 square millimeters.

Lead 10 includes a connector assembly 28 positioned at proximal end 14 of lead 10. Connector assembly 28 includes two sets of sealing rings 38 for forming a fluid tight-seal within a connector bore of an associated implantable pacemaker. A connector pin 32 is electrically coupled via a conductor extending through lead body 16 to tip electrode 20. Connector ring 30 is electrically coupled to coil electrode 18 via a second conductor extending through lead body 16.

A guidewire or stylet may be used to aid in deploying lead 10. A guidewire 34 is shown entering proximal end 14 of lead 10 through hollow connector pin 32 and exiting the distal tip electrode 20 through seal 24. The lead body 16 may be preformed with a curve or bend 26 to aid in guiding the lead to a desired implant site. A guidewire or stylet may be used to straighten lead 10 or to adjust the curvature of distal end 12 of lead 10.

While lead 10 is shown having a single coil electrode 18, other embodiments could include two or more coil electrodes spaced at desired locations along the length of lead body 16. For example, when the lead 10 is positioned deep in a cardiac vein for left ventricular pacing and/or sensing, another coil electrode could be positioned more proximally from coil electrode 18 to provide pacing and/or sensing in the left atrium. FIG. 2 illustrates a multi-polar cardiac vein lead having tip electrode 20 and three flexible coil electrodes 18,19 and 21 for achieving bipolar pacing and/or sensing in the left ventricle and in the left atrium. The multi-polar lead of FIG. 2 includes some of the same elements numbered identically as in lead 10 of FIG. 1.

Coil electrode 18 may serve as an anode paired with the cathode tip electrode 20 as described above in conjunction with FIG. 1. Coil electrodes 19 and 21 may serve as a bipolar pair for pacing and/or sensing in the left atrium or as a bipolar pair for pacing and/or sensing a second site along the left ventricle. The size of each coil electrode 18, 19, and 21 may be adjusted according to its intended purpose. For example, a relatively shorter coil electrode 19 may be provided, reducing the electrode surface area and thereby increasing pacing impedance, to serve as an anode paired with a relatively longer coil electrode 21 to serve as a cathode for pacing in the left atrium.

Each coil electrode 18, 19 and 21 is coupled via a corresponding conductor extending within lead body 16 to a corresponding ring connector 30, 35 or 37 included in a proximal, quadrapolar connector assembly 29. Multiple sets of sealing rings 38 serve to seal the connector assembly within the bore of an associated pacemaker and prevent fluid leakage between connector rings 30, 35 and 37 and connector pin 32. Tip electrode 20 is coupled, via a corresponding conductor, to connector pin 32. The conductors extending within lead body 16 may be arranged concentrically with intervening layers of insulation, as generally described in U.S. Pat. No. 4,355,646 issued to Kallok, incorporated herein by reference in its entirety. Alternatively, lead body 17 may be provided as a multi-lumen lead body for carrying multiple conductors corresponding to each electrode 18,19, 21, and 22. A suitable multi-lumen lead body is disclosed in U.S. Pat. No. 5,584,873 issued to Shoberg et al., incorporated herein by reference in its entirety.

FIG. 3 is a side, cut-away view of a distal end of a lead having a flexible coil electrode in accordance with the present invention. As illustrated in FIG. 3, lead body 16 includes an outer insulation sheath 40 and an inner insulation sheath 42. Outer and inner insulation sheaths 40 and 42 are preferably formed from a biocompatible polymer such as polyurethane or silicone rubber. In a preferred embodiment, outer sheath 40 is formed from polyurethane and inner sheath 42 is formed from silicone rubber. Outer insulation sheath 40 is discontinuous in the region of coil electrode 18, exposing electrode 18 to the surrounding tissue. Coil electrode 18 is electrically coupled to a conductive sleeve 48 by welding, crimping or another appropriate method. Sleeve 48 is formed from a biocompatible conductive metal such as stainless steel, platinum, or platinum alloys. The length of sleeve 48 is preferably minimized to limit the rigid length imposed on lead body 16. For example, the length of sleeve 48 is preferably no longer than the rigid length of tip electrode 20, extending from a proximal end 23 of electrode 20 to a distal end 25 of electrode 20, such that sleeve 48 is not a limiting factor in maneuvering lead 10 through a tortuous pathway. Conductive sleeve 48 is further electrically coupled to a coiled conductor 44, which extends to connector ring 30 on proximal connector assembly 28.

A flexible polymer tube 50 may be provided inside the inner diameter of coil electrode 18 to provide structural support to coil electrode 18. Polymer tube 50 is preferably bonded to outer insulation sheath 40 in areas where tube 50 and sheath 40 overlap. An adhesive, such as silicone adhesive, may also be used to back fill open areas between windings of coil electrode 18 to provide a smooth surface on the outer diameter of coil electrode 18.

Inner insulation sheath 42 surrounds a coiled conductor 46 that is electrically coupled to tip electrode 20. Seal 24 is molded onto internal sleeve 52, which is preferably formed from a rigid, biocompatible, conductive material such as stainless steel, titanium, platinum, or titanium or platinum alloys. Internal sleeve 52 may alternatively be formed from a rigid, biocompatible, non-conductive material, such as polyurethane, Delrin or other high durometer polymer. Internal sleeve 52 is provided with an annular, laterally extending flange 54. Seal 24 is retained by the interaction of flange 54 and tip electrode 20. Internal sleeve 52 may act as a crimp core for crimping the shaft 56 of tip electrode 20 around coiled conductor 46 to establish electrical connection of tip electrode 20 to conductor 46. A guidewire or stylet may be advanced through the center lumen of coiled conductor 46 and through internal sleeve 52 and seal 24.

Conductors 44 and 46 are shown as concentrically arranged coiled conductors and may be formed of MP35N alloy wire. Conductors 44 and 46 may alternatively be provided in the form of any of the numerous conductor types known for use in conjunction with cardiac pacing leads such as cabled or stranded conductors, for example as disclosed in U.S. Pat. No. 5,246,014, issued to Williams et al., incorporated herein by reference in its entirety, or non-concentric coils enclosed in a bitumen lead body, or a multi-filar coiled conductor wherein individual filars are insulated from each other and serve as separate conductors as disclosed in U.S. Pat. No. 4,944,088 issued to Doan, et al., incorporated herein by reference in its entirety.

Figure 3A:
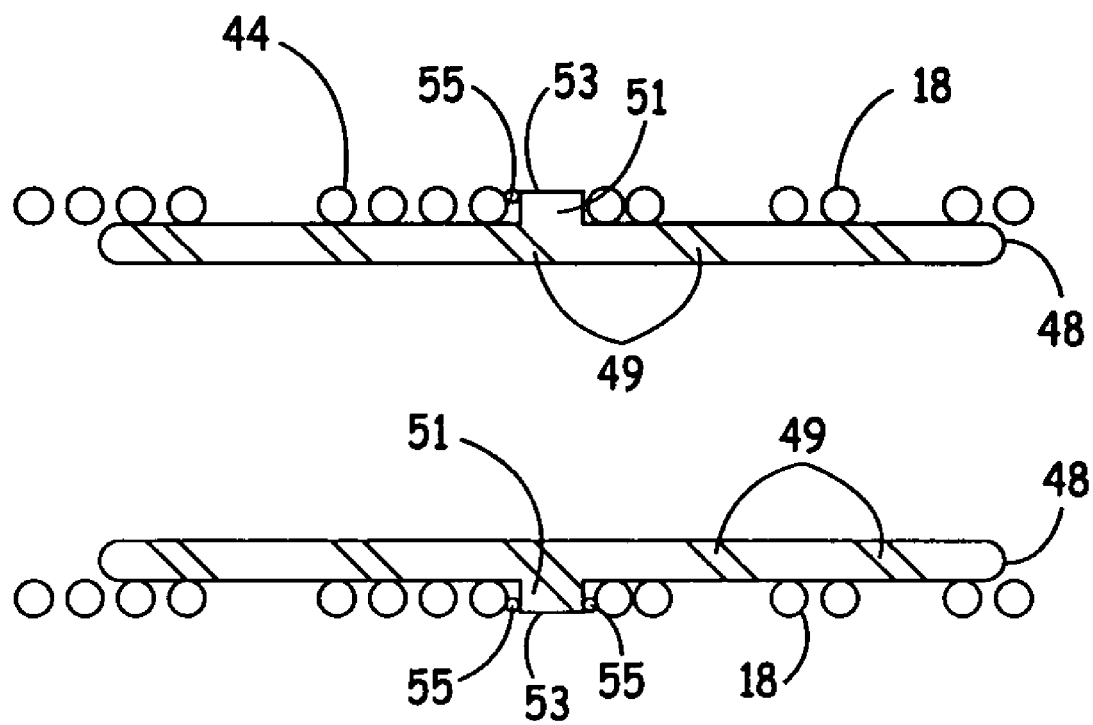
FIG. 3A is a side, cut-away view of a conductive sleeve of a lead according to an alternate embodiment of the present invention.

FIG. 3A is a side, cut-away view of a conductive sleeve of a lead according to an alternate embodiment of the present invention. As illustrated in FIG. 3A, according to an alternate embodiment of the present invention, sleeve 48 is provided with further flexibility by incorporating helical cuts, corrugations or other flexing mechanisms in sleeve 48. For example, according to the alternate embodiment of the present invention, spaced groove portions 49 are formed along sleeve 48 to provide sleeve 48 with increased flexibility. In addition, coiled conductor 44 is coupled to a flange portion 51 of sleeve 48, using known coupling techniques, such as welding techniques, for example, to form a weld 55 along an upper portion 53 of flange 51, fixedly engaging coiled conductor 44 to sleeve 48 at flange portion.

According to a preferred embodiment of the present invention, groove portions 49 are cut at an angle corresponding to a pitch of coil electrode 18 in order to maximize the resulting flexibility of coiled conductor 18. However, it is understood that the present invention is intended to include groove portions 49 cut at any desired angle.

Figure 4:
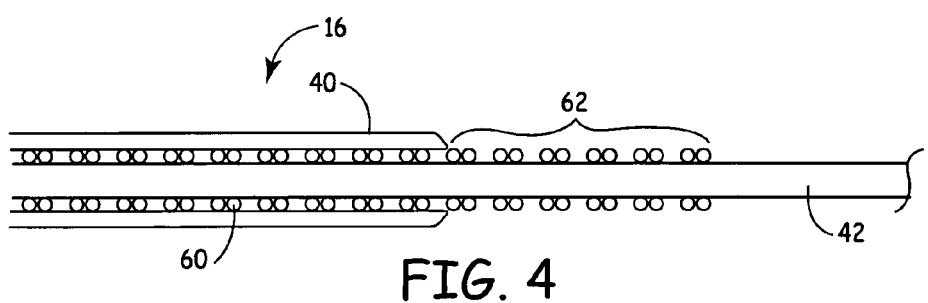
FIG. 4 is side, cut-away view of an alternate embodiment of a coil electrode assembly according to the present invention.

FIG. 4 is side, cut-away view of an alternate embodiment of a coil electrode assembly according to the present invention. As illustrated in FIG. 4, according to an alternate embodiment of the present invention, outer insulation sheath 40 is terminated exposing a distal segment 62 of a coiled conductor 60 that serves as a coil electrode. Exposed distal segment 62 of conductor 60 may serve as an anode or cathode with the exposed area corresponding to exposed distal segment 62 of conductor 60 varied depending on the desired electrode function of distal segment 62. By providing a flexible coil electrode as exposed distal segment 62 of conductor 60, the present invention advantageously eliminates any rigid components needed for assembly of lead 10, thus maintaining lead flexibility, reducing cost, and easing manufacturing processes.

Coiled conductor 60 and electrode 62 are preferably formed from platinum iridium clad tantalum wire. Coil electrode 62 may resemble an outer conductor/indifferent electrode as generally disclosed in U.S. Pat. No. 6,321,123 B1, issued to Morris et al., incorporated herein by reference in its entirety.

Figure 5:
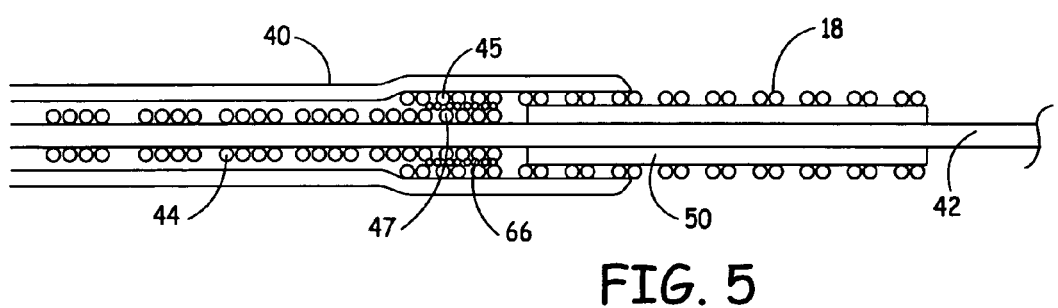
FIG. 5 is a side, cut-away view of an alternate embodiment of a coil electrode assembly of a lead according to the present invention.

FIG. 5 is a side, cut-away view of an alternate embodiment of a coil electrode assembly of a lead according to the present invention. As illustrated in FIG. 5, according to an alternate embodiment of the present invention, a proximal end 45 of coil electrode 18 extends over a distal end 47 of coiled conductor 44 to form an overlap area 66, so that coil electrode 18 and coiled conductor 44 are electrically coupled directly to each other along overlap area 66 using welding techniques, for example. This method of assembly also eliminates additional rigid piece parts thus maintaining flexibility of the distal lead end. Outer insulation sheath 40 is discontinuous, exposing coil electrode 18 to the surrounding tissue. A polymer tube 50 positioned inside coil electrode 18 provides structural support and may be bonded to outer sheath 40.

Figure 6:
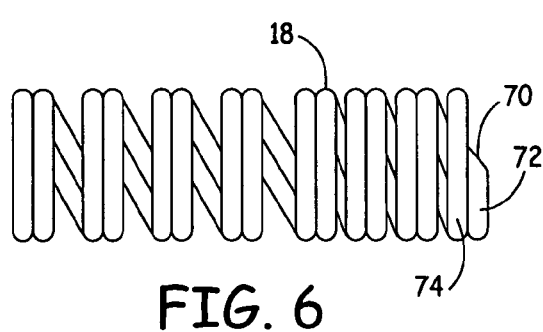
FIG. 6 is a side view of a coil electrode illustrating a method for finishing ends of a flexible coil electrode, according to the present invention.

FIG. 6 is a side view of a coil electrode illustrating a method for finishing ends of a flexible coil electrode, according to the present invention. According to the present invention, each filar included in a bifilar coil is trimmed at a distal end and may be sculpt welded onto an adjacent filar. For example, as illustrated in FIG. 6, a distal end 70 of a filar 72 is welded to a filar 74 adjacent to filar 72.

Figure 7:
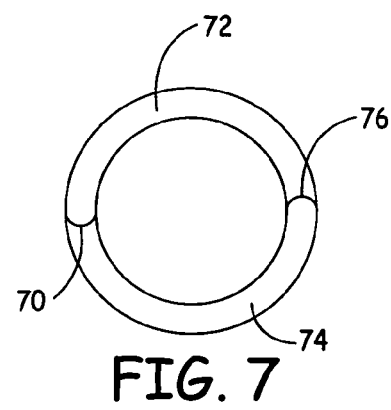
FIG. 7 is front view of a coil electrode according to the present invention.

FIG. 7 is front view of a coil electrode according to the present invention. As illustrated in FIGS. 6 and 7, distal end 70 of filar 72 is trimmed and welded against filar 74. Filar 74 is trimmed at distal end 76, which is welded against filar

72. Finishing the ends of coil electrode 18 in this way removes sharp edges and prevents the distal ends of filars 72 and 74 from becoming caught on anatomic structures during lead deployment. The proximal ends of filars 72 and 74 may be finished in the same manner as just described. However, finishing the proximal ends of the filars may not be necessary because the proximal ends may be contained within a weld pool when the proximal end of the coil electrode is welded to a conductor, as described in conjunction with FIG. 5, or to a conductive sleeve, as described in conjunction with FIG. 3.

Figure 7A:
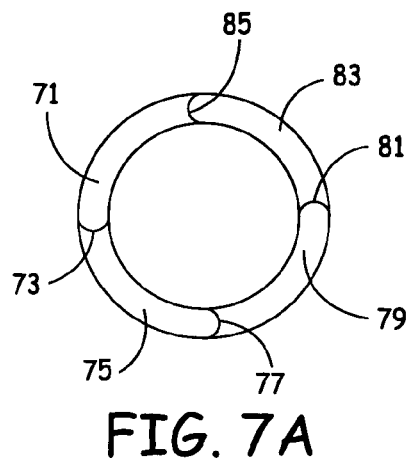
FIG. 7A is a front view of a coil electrode according to the present invention.

FIG. 7A is a front view of a coil electrode according to the present invention. As illustrated in FIG. 7A, if coil electrode is a quadrafilar coil, including a first filar 71 having a distal end 73, a second filar 75 having a distal end 77, a third filar 79 having a distal end 81, and a fourth filar 83 having a distal end 85, distal end 73 is trimmed and welded against filar 75, distal end 77 is trimmed and welded against filar 79, distal end 81 is trimmed and welded against filar 83 and distal end 85 is trimmed and welded against filar 71. It is understood that although conductor coil 18 is shown as being either a bifilar or quadrafilar coil, conductor coil 18 of the present invention could include any number of filars. In addition, welding of distal ends of filars described above is preferably performed using laser welding, although other welding techniques may also be utilized.

Figure 8:
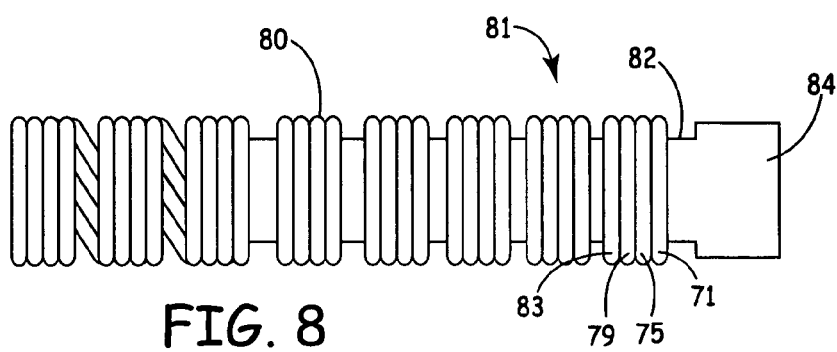
FIGS. 8 and 9 illustrate an alternative method for fixedly positioning an end of a flexible coil electrode, according to the present invention.
Figure 9:
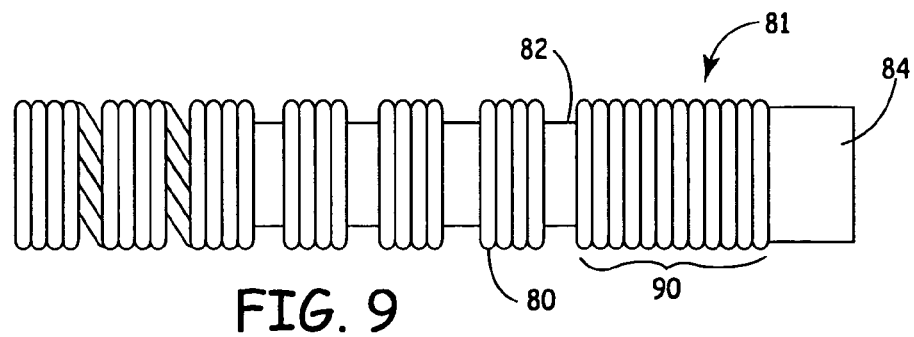

FIGS. 8 and 9 illustrate an alternative method for fixedly positioning an end of a flexible coil electrode, according to the present invention. As illustrated in FIGS. 8 and 9, according to a preferred embodiment of the present invention, a multi-filar coil electrode 80 is mounted on a mandrel 82 that includes a handle 84. Coil electrode 80 is advanced along mandrel 82 towards handle 84 so that a distal end portion 81 of coil electrode 80 is compressed against handle 84 as illustrated in FIG. 9 to form compressed filars 90 that are then joined by a continuous, radial weld. In this way, loose ends 73, 77, 81, 85 of each of filars 71, 75, 79, 83, respectively, are constrained within the weld pool and prevented from extending in a way that may cause damage to filars 71, 75, 79, 83 or to surrounding tissue or lead components. Prior to the welding process, ends 73, 77, 81, 85 of filars 71, 75, 79, 83 are preferably ground flush such that all of filars 71, 75, 79, 83 end in a single cross-sectional plane. Filars 71, 75, 79, 83 are ground flush, for example, by placing the distal end portion 81 of coil electrode 80 perpendicularly against a grinding wheel mounted on a rotary tool. Once ground flush, corresponding ends 73, 77, 81, 85 of filars 71, 75, 79, 83 are welded to adjacent filars, as described above in reference to FIG. 7A. The method depicted in FIGS. 8 and 9 is particularly advantageous when coil electrode 80 is formed from a multi-filar coil since each individual filar end does not need to be singly identified and welded.

The mandrel 82 is preferably formed from a material that allows coil electrode 80 to be easily removed after welding is performed. Furthermore, the mandrel 82 is preferably formed from a material that will not contaminate the weld pool. A preferred mandrel material is molybdenum. Other materials, such as copper, have been found to leave contaminates in the weld pool and may adhere to the welded area of the coil making removal of the coil from the mandrel difficult.

Thus, a bipolar or multi-polar cardiac vein lead having flexible coil electrode(s) and method for assembly have been described. Aspects of the inventive lead system may be included in various catheter deliverable or "over-the-wire" medical leads. The embodiments described herein, therefore, should be considered exemplary and not limiting with regard to the following claims.

We claim:

1. A cardiac pacing lead, comprising:
    an elongated lead body extending from a proximal end to a distal end, the lead body having an outer insulative sheath;
    a first electrode positioned at the distal end of the lead body;
    a second electrode spaced proximally from the first electrode and positioned within the outer insulative sheath, wherein the second electrode includes a plurality of filars having corresponding distal ends, each of the distal ends being fixed to a corresponding adjacent filar of the plurality of filars,
    a conductive sleeve electrically coupled to the second electrode; and
    a conductor extending from the proximal end of the lead and electrically coupled to the conductive sleeve, wherein the sleeve has a first length, the first electrode has a second length, and the first length is not greater than the second length, and wherein the conductive sleeve includes spaced grooved portions.

2. The cardiac pacing lead of claim 1, wherein the outer insulative sheath is discontinuous in a region corresponding to the second electrode.

3. The cardiac pacing lead of claim 1, wherein the grooved portions are positioned along the conductive sleeve at an angle corresponding to a pitch of the second electrode.

4. The cardiac pacing lead of claim 1, further comprising a conductor extending within the lead body from the proximal end of lead body to the distal end of lead body, wherein the outer insulation sheath terminates along a portion of the conductor corresponding to the second electrode.

5. The cardiac pacing lead of claim 1, further comprising a conductor extending within the lead body from the proximal end of lead body to the distal end of lead body, wherein a proximal end of the second electrode extends along a distal end of the conductor to form an overlap area, the second electrode and the conductor being electrically coupled along the overlap area.

6. A cardiac pacing lead according to claim 1, wherein the second electrode is formed of one of a platinum material, an iridium material, a titanium material and an alloy of platinum, iridium, and titanium materials.

7. A cardiac pacing lead according to claim 1, wherein the distal ends are fixed to the corresponding adjacent filar using a laser welding technique.

8. A cardiac pacing lead according to claim 1, further comprising a tube, extending within an inner portion of the second electrode, providing structural support of the second electrode.

9. A cardiac pacing lead, comprising:
    an elongated lead body extending from a proximal end to a distal end, the lead body having an outer insulative sheath;
    a first electrode positioned at the distal end of the lead body; and
    a second electrode spaced proximally from the first electrode and positioned within the outer insulative sheath, wherein the second electrode includes a plurality of filars having corresponding distal ends, each of the distal ends being fixed to a corresponding adjacent filar of the plurality of filars, wherein the plurality of filars includes a first filar having a first filar distal end, a second filar having a second filar distal end, a third filar having a third filar distal end, and a fourth filar having a fourth filar distal end, and wherein the first filar distal end is trimmed and fixedly engaged with the second filar to be positioned proximal from the second distal end, the second filar distal end is trimmed and fixedly engaged with the third filar to be positioned proximal from the third distal end, the third filar distal end is trimmed and fixedly engaged with the fourth filar to be positioned proximal from the fourth distal end.

10. A cardiac pacing lead, comprising:

an elongated lead body extending from a proximal end to a distal end, the lead body having an outer insulative sheath;

a first electrode positioned at the distal end of the lead body; and a second electrode spaced proximally from the first electrode and positioned within the outer insulative sheath, wherein the second electrode includes a plurality of filars having corresponding distal ends, each of the distal ends being fixed to a corresponding adjacent filar of the plurality of filars, wherein the second electrode has a first surface area of approximately 30 to 40 square millimeters and the first electrode has a second surface area of approximately 5 to 6 square millimeters.

11. A cardiac pacing lead, comprising:

an elongated lead body extending from a proximal end to a distal end, the lead body having an outer insulative sheath;

a first electrode positioned at the distal end of the lead body; and a second electrode spaced proximally from the first electrode and positioned within the outer insulative sheath, wherein the second electrode includes a plurality of filars having corresponding distal ends, each of the distal ends being fixed to a corresponding adjacent filar of the plurality of filars and positioned proximal to a distal end of the adjacent filar, wherein the second electrode is formed from a bifilar platinum iridium coil.

12. A method of forming a cardiac lead having an elongated lead body extending from a proximal end to a distal end, the lead body having an outer insulative sheath, comprising the steps of:

positioning a first electrode along the distal end of the lead body;

positioning a second electrode within the outer insulative sheath to be spaced proximally from the first electrode;

advancing the second electrode along a mandrel so that a distal end portion of the second electrode is engaged against a handle of the mandrel to form fixedly engaged compressed filars; and fixedly coupling corresponding distal ends of a plurality of filars corresponding to the compressed filars to a corresponding adjacent filar of the plurality of filars.

13. The method according to claim 12, further comprising the step of forming the distal ends to be flush along a single cross-sectional plane.

14. The method according to claim 12, wherein the mandrel is formed of molybdenum.

15. A cardiac pacing lead, comprising:

an elongated lead body extending from a proximal end to a distal end, the lead body having an outer insulative sheath; and an electrode positioned within the outer insulative sheath, wherein the electrode includes a first filar having a first filar distal end, and a second filar having a second filar distal end, and wherein the first filar distal end is trimmed and fixedly engaged with the second filar to be positioned proximal from the second filar distal end, and the second filar distal end is trimmed and fixedly engaged with the first filar.

* * * * *